US011545258B2

(12) United States Patent
Ulloa

(10) Patent No.: US 11,545,258 B2
(45) Date of Patent: Jan. 3, 2023

(54) SYSTEM AND METHOD FOR FACILITATING DATA ACCESS FOR ITINERATE MEDICAL PERSONNEL

(71) Applicant: Jeannette Ulloa, Irving, TX (US)

(72) Inventor: Jeannette Ulloa, Irving, TX (US)

(73) Assignee: CRE-Dense Upload, Inc., Irving, TX (US)

(\*) Notice: Subject to any disclaimer, the term of this patent is extended or adjusted under 35 U.S.C. 154(b) by 485 days.

(21) Appl. No.: 16/752,145

(22) Filed: Jan. 24, 2020

(65) Prior Publication Data

US 2021/0233649 A1 Jul. 29, 2021

(51) Int. Cl.
*G06Q 40/08* (2012.01)
*G06Q 50/18* (2012.01)
*G16H 40/20* (2018.01)

(52) U.S. Cl.
CPC .................................. *G16H 40/20* (2018.01)

(58) Field of Classification Search
CPC ...................................................... G16H 40/20
See application file for complete search history.

(56) References Cited

U.S. PATENT DOCUMENTS

| 2004/0204948 | A1 | 10/2004 | Singletary et al. |
| 2009/0177511 | A1 | 7/2009 | Shaw et al. |
| 2011/0055099 | A1 | 3/2011 | Paul et al. |
| 2015/0310188 | A1\* | 10/2015 | Ford ............... G06F 21/10 726/28 |
| 2018/0301218 | A1 | 10/2018 | Bochaton |

FOREIGN PATENT DOCUMENTS

WO 2006020570 A2 2/2006

OTHER PUBLICATIONS

Praos Health Inc., "Mobilizing your Nursing Workforce", https://praoshealth.com, Downloaded on Jan. 24, 2020, 4 pages.

\* cited by examiner

*Primary Examiner* — Maroun P Kanaan
(74) *Attorney, Agent, or Firm* — St. Onge Steward Johnston and Reens LLC

(57) ABSTRACT

A system and method for securely allowing access to personal medical worker information for itinerate medical workers working on a contract basis for various medical facilities. The system includes a medical personnel records computer designed to interface with a medical facility computer when a medical worker selects a work contract associated with the medical facility. The medical worker's personal information is selectively shared based on user defined rules to limits potential compromising of the medical workers personal data due to a data breach or the like.

20 Claims, 13 Drawing Sheets

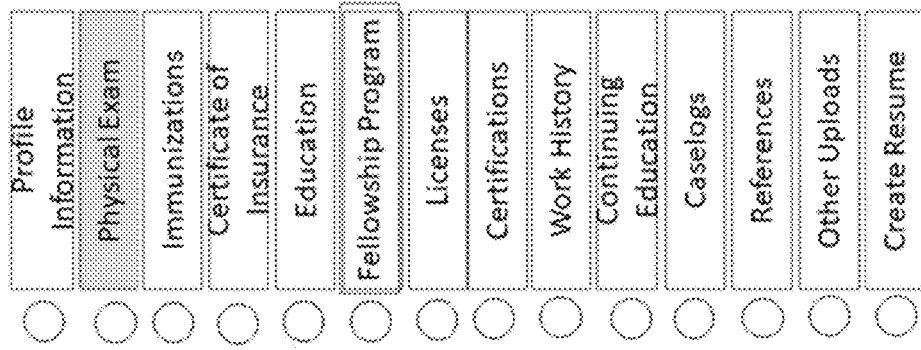
FIG. 6

Certifications:
- Professional Certification:
  - Primary specialty
  - Issuing Agency:
  - Issued Date:
  - Expiration Date:
- ACLS:
  Expiration Date:
- PALS:
  Expiration Date:
- BLS:
  Expiration Date:
- NRP:
  Expiration Date:
- Trauma:
  Expiration Date:
- Other Certifications:
  Expiration Date:

○ Profile Information
○ Physical exam
○ Immunizations
○ Certificate of Insurance
○ Education
○ Fellowship Program
○ Licenses
○ Certifications
○ Work History
○ Continuing Education
○ Caselogs
○ References
○ Other Uploads
○ Create Resume

*FIG. 12*

Work experience

Previous Practice/Employer name:

Start/End Dates:

Address:

Contact information:
* Name
* Phone number
* Email address:

Profile Information | Physical exam | Immunizations | Certificate of Insurance | Education | Fellowship Program | Licenses | Certifications | Work History | Continuing Education | Caselogs | References | Other Uploads | Create Resume

*FIG. 13*

SYSTEM AND METHOD FOR FACILITATING DATA ACCESS FOR ITINERATE MEDICAL PERSONNEL

FIELD OF THE INVENTION

A system and method for facilitating the inter-facility movement of medical personnel, and more particularly, the invention is directed to a system and method for assisting itinerate medical personnel in providing the needed documentation to medical facilities prior to beginning contract work for the medical facility.

BACKGROUND OF THE INVENTION

In the medical industry in the United States, itinerate medical personnel regularly pick up contracts to work for different medical facilities across the country for a set period of time. For example, a registered nurse, a physician's assistance or a medical doctor may contract to work for a hospital for a period of two months. Alternatively, the length of the contract could be a short as one or two weeks or for a longer period of time. However, each facility requires specific documentation.

The strict licensing requirements and documentation required to be provided to the medical facility that is contracting with the medical personnel for the contract period is no lower than that required for a permanent hire. In other words, the documentation required is intensive and may include: 1) proof of education (e.g., graduate of accredited medical school, graduate of accredited nursing program, etc.); 2) proof of licensing and all certifications (e.g., medical license in the state, nursing license/credentials in the state, pediatrics certifications, etc.); 3) proof of insurance (e.g., malpractice insurance, etc.); 4) documentation relating to any malpractice claims made against the individual; and 5) proof of immunizations/physicals/health status and so on. As such, the documentation requirements can be extremely burdensome especially when the number of different contracts picked up by the person is relatively large.

All of this documentation must be transmitted ahead of time to each and every hospital or medical facility the individual will work in. In particular, the documentation must arrive with enough time to allow for facilities personnel to verify the information and allow time for correction of any missing or incomplete information. When an individual picks up 10-12 contracts over the course of a year, each of which may be located at diverse locations across the United States where each medical facility and each state may have their own documentation requirements, the documentation burden can become unwieldy.

Another issue is that there is no uniformity between medical facilities with respect to the form of the documentation and the specific required information. In other words, each medical facility may require documentation to be submitted in a specific format and the information may need to be modified to fit that. Additionally, the particular information required by a particular facility may vary from facility to facility.

Still another issue is that with the increase in the number of data breaches on the rise, the sharing of personal information increases the risk that personal data may be compromised. The documentation needed by various medical facilities contains personal information, such as licensure, certificate of liability and other credentialing documents. Transmission of this information via plain text email creates a risk of the information being compromised.

The risk of personal information being compromised becomes even clearer when the credentialing process is analyzed. Information is first sent to a third-party company that validates the credentials before being forwarded to the hospital. Often a hospital will require additional information to be sent directly to the hospitals' credentialing team. The exchange creates multiple opportunities for the information to be compromised, as it is passed between the individual, the third-party company, and the hospital.

This risk is increased for itinerate medical workers who contract with multiple facilities during the year and therefore must share sensitive personal information with multiple facilities in connection with each work contract. Still further, as the medical worker moves on to their next contracted work assignment, the medical facility may retain access to the medical worker's personal data even when they have completed their contract. As such, itinerate medical workers have an interest in sharing only a selected amount of personal data as needed by the medical facility and in only allowing access to their personal data for a specified time period.

SUMMARY OF THE INVENTION

In view of the above, a goal of the system is to provide a secure platform that is easy for a user to add documentation to while storing the documentation securely. Since the documentation is stored within the system securely, the user can modify and adjust the documentation for future credentialing needs. The application allows the user to create secure links for the parties involved to review and validate the credentials.

What is desired is a system and method for sharing itinerate medical personnel information with a medical facility that allows for a medical worker to remotely and automatically share personal information with the facility.

It is further desired to provide a system and method that allows for itinerate medical personnel to automatically share only specifically selected personal data with a medical facility and to automatically limit the duration for which the medical facility has access to that information.

It is still further desired to provide a system and method that provides for the automatic uploading of personal information relating to itinerate medical personnel that automatically is adjusted to meet the data and formatting requirements of a medical facility with which the medical worker has contracted.

Finally, it is desired to provide a system and method for automatically generating medical credentials for an individual when personal medical data associated with the individual is received and processed by a medical facility and meets the medical facilities requirements.

The current system is directed to system to facilitate the automatic access to documentation for a medical worker by a medical facility governed by rules set up by the medical worker and a set of rules established by the medical facility. In one configuration, a medical documentation computer is provided having a network connection and a storage accessible by the computer. A medical worker has access to the medical documentation computer via a user computer that is connected to the network. The user can upload their personal information to be saved on the storage for access by medical facilities. A medical contract company acts as a broker between various medical facilities and the medical worker to present various medical contracts associated with the various medical facilities. The medical contract company utilizes a medical contract computer connected to the network and provided with a storage having medical contract data stored thereon representative of various proposed medical worker contracts. The medical worker can access the various proposed medical worker contracts to be bid on or selected. Once the medical worker selects a particular contract, the medical contract computer can send an indication to the medical facility computer that an individual has selected a contract.

In one configuration, once a contract is selected, the medical worker could then log onto the medical documentation computer and can select what personal information is to be shared with the medical facility associated with the contract that was selected. Alternatively, the act of selecting the contract can function as an "approval" on the part of the user to allow the medical facility associated with the contract to access the information required by the medical documentation computer.

It is understood that the medical facility associated with the contract can have specific information requirements that may be unique to or differ from other medical facilities data requirements. Still further, the medical facility may require the data to be provided in a certain type of format. As such, in one configuration it is contemplated that a medical facility can log into the medical documentation computer and provide a set rules reflective of a format of the medical personnel data. This rule set that is provided on the medical documentation computer, could be programmable and selectable for each medical facility so that specific information provided and a format in which the specific information is provided is fully customizable. In this configuration, the user, upon selection of a contract, can log onto the medical documentation computer and see precisely what information the medical facility will require and can enable access to that information. Alternatively, the user could automatically allow access to the information required by the medical facility associated with the selected contract.

Additionally, in one configuration a window of time may be provided within which the medical facility will have access to the information associated with the medical worker. For example, the access could range from between 24-72 hours, after which the access to the information through the medical documentation computer is no longer available. It is further contemplated that any medical facility that seeks access to medical documentation associated with a user will have to comply with the Health Insurance Portability and Accountability Act (HIPAA) requirements. For example, medical facilities accessing the medical documentation of medical workers would need to utilize certificate-based encryption for access and/or transfer of data. In one configuration, no personal data of the medical worker would be allowed to be copied from the medical documentation computer, but rather, only access (for a specified duration) would be allowed. In other configurations, certain data may be allowed to be transferred but under very tight security.

Once all the needed documentation is accessed and evaluated by the medical facility and it is determined that all documentation is in order, only then would the medical facility system facilitate the producing of medical credentials for the medical worker to work at the medical facility associated with the particular contract. Generation of the credential could include, in one configuration, automatically creating or printing a badge that is wearable by the medical worker for the duration of the contract. The badge could include a picture of the individual, the pertinent information the medical facility would require on the badge and a scannable code that would include the time period for which the badge was valid.

The system provides several distinct advantages over known ways of providing personal medical information for workers to medical facilities. For example, when the user is ready to send a completed application to a third party or hospital for validation, the software generates a time limited link that generates a custom packet for the party to review in order to complete validation. This may be done manually or automatically through the rules set up by the user. The system may utilize secure socket layer technology in conjunction with encryption to ensure that the data is only accessible by the party that is responsible for the validation. Encryption used is based on the Advanced Encryption Standard (AES) algorithm.

The system also provides secure pdf/image storing techniques that ensures the data can't be accessed outside of the application. All of the documentation is stored in a folder that requires secure access. To further increase security of the files, they are validated against base 64 to ensure they have not been compromised. Files are also assigned names that carry no relevant information as to what the file contains. Information on the file is stored security in the database for the software to be able to access, decrypt and process the file.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, applications, media, components, networks, systems, subsystems, and/or means, constituting any one or more of (a) a connection, whether direct or through one or more other devices, apparatus, files, programs, applications, media, components, networks, systems, subsystems, or means, (b) a communications relationship, whether direct or through one or more other devices, apparatus, files, programs, applications, media, components, networks, systems, subsystems, or means, and/or (c) a functional relationship in which the operation of any one or more devices, apparatus, files, programs, applications, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, routing of data, modification of data, formatting and/or conversion of data, tagging or annotation of data, measurement, comparison and/or review of data, and may or may not comprise a program.

In one configuration a system for selectively controlling access to medical personnel data is provided comprising a medical personnel records computer having a storage and coupled to a network where the medical personnel records computer is adapted to receive medical personnel data associated with a user and saved on the storage. The system is provided such that the user sets user defined rules governing access to the medical personnel data associated with the user. The system is further provided such that the user accesses a medical contract computer having a plurality of proposed medical contracts each associated with a medical facility and the user selects at least one of the plurality of proposed medical contracts. The medical contract computer is coupled to a medical facility computer associated with the medical contract selected by the user, and the medical contract computer transmits data relating to the user selected contract. The system is also provided such that the medical facility computer couples to the medical personnel records computer in response to receipt of the data relating to the user selected contract, and the medical facility computer having medical facility defined rules. Finally, the systems provides that the medical personnel records computer selectively allows access to the medical personnel data associated with the user according to the user defined rules, and the medical personnel records presents medical personnel data associated with the user to the medical facility computer based on the user defined rules and the medical facility defined rules.

In another configuration a method for selectively controlling access to medical personnel data is provided comprising the steps of accessing a medical personnel records computer and uploading medical personnel data associated with a user to be saved on a storage accessible by the medical personnel records computer, setting user defined rules governing access to the medical personnel data associated with a user and accessing a medical contract computer having a plurality of proposed medical contracts each associated with a medical facility. The method further comprises the steps of selecting at least one of the plurality of proposed medical contracts, transmitting the selection from the medical contract computer to a medical facility computer associated with the medical contract selected by the user and requesting medical personnel data associated with a user be accessed by the medical facility computer. Finally the method comprises the steps of granting the access request of the medical facility computer to access the medical personnel data associated with a user when the user defined rules allow for such access and generating medical credentials when the accessed medical personnel data associated with a user is compliant with a medical facility defined set of rules.

Other objects of the invention and its particular features and advantages will become more apparent from consideration of the following drawings and accompanying detailed description.

BRIEF DESCRIPTION OF THE DRAWINGS

FIGS. 5-13 are various screen shots of the system allowing for the uploading of information by the user to create medical personnel data associated with a user according to the system of FIG. 1.

DETAILED DESCRIPTION OF THE INVENTION

Figure 1:
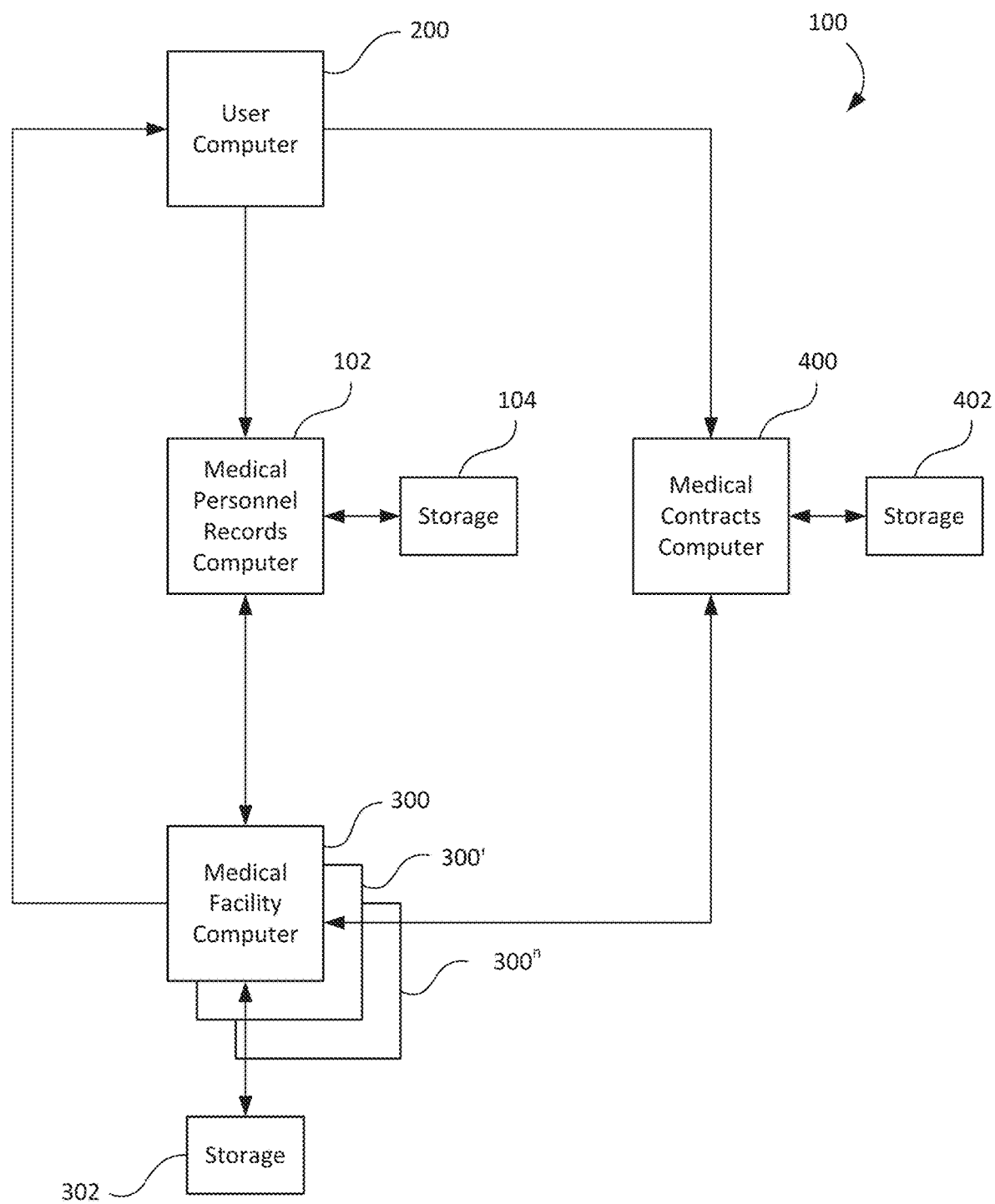
FIG. 1 is a block diagram of a system according to one configuration of the invention.

Referring now to the drawings, wherein like reference numerals designate corresponding structure throughout the views.

FIG. 1 depicts the system 100 for selectively controlling access to medical personnel data. The system 100 includes a medical personnel records computer 102 that includes a storage 104 on which medical personnel data associated with a user is stored.

A user computer 200 may be utilized by a user to access a medical personnel records computer 102 via a network connection. The medical personnel records computer 102 is adapted to receive medical personnel data associated with a user, which can be saved on storage 104. Additionally, a user can set up rules governing the sharing of the medical personnel data associated with a user, which are also saved on storage 104.

Also shown in FIG. 1 is a medical facility computer 300 having an associated storage 302 and a medical contracts computer 400, also having an associated storage 402. A plurality of medical facility computers 300, 300', 300" are depicted to illustrate than many medical facilities will be accessing and posting contracts on medical contracts computer 400. Each medical facility will have their own specific information that they will want to received in connection with their contracts and may want to access the information in a specific file format(s).

A medical facility looking to hire itinerate medical workers can log onto the medical contracts computer 400 and save proposed medical contracts thereon. The medical facility computer 300 can also log onto the medical personnel records computer 102 and set up a set of rules governing the type and format of medical personnel data that should be received associated with each of the various proposed medical contracts that have been posted. In one embodiment, the type of medical personnel data can include, for example, education information, licensing information, certification information, insurance information, malpractice information, immunization information, health status information and so on. Additionally, the formatting rules are provided to govern a file format in which the medical personnel data is provided to the medical facility.

Figure 2:
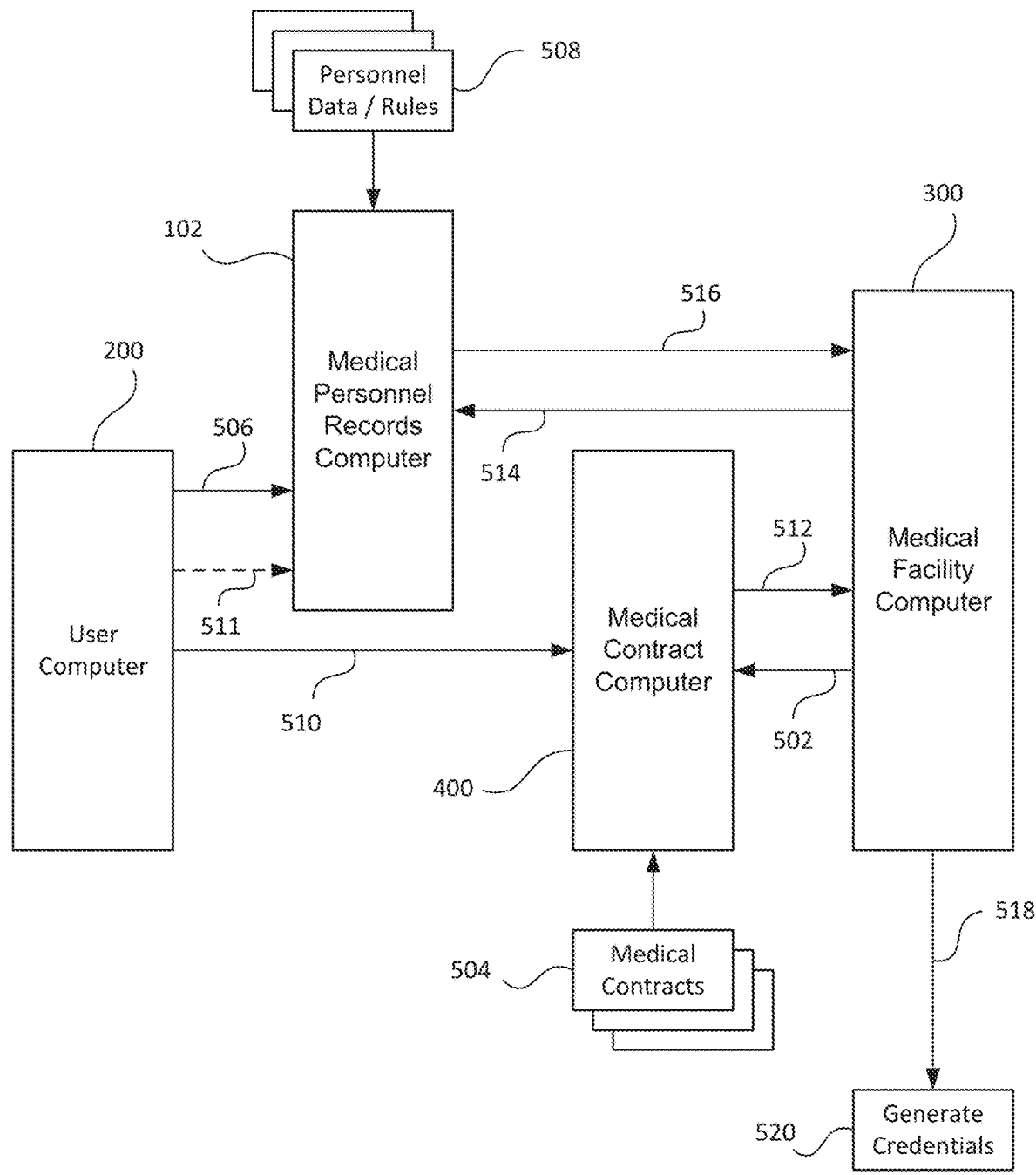
FIG. 2 is a block diagram illustrating the functioning of the system according to FIG. 1.

FIG. 2 illustrates the functional interchange of information that is shared between the user computer 200, the medical personnel records computer 102, the medical facility computer 300 and the medical contracts computer 400. As previously stated, the medical facility computer 300 is a computer associated with a medical facility that is providing proposed contracts for medical workers to come and work at the medical facility for a specified period of time. The medical contracts computer 400 is associated with a third party that acts as a broker for medical contracts between the medical facility and medical workers.

As an initial step, a medical facility will upload or transmit 502 a proposed medical contract to medical contracts computer 400. This proposed contract or a plurality of contracts 504 will then be viewable to any medical worker logging onto medical contracts computer 400.

Also as an initial step, a medical worker (user) will upload or transmit 506 medical personnel data associated with the user from user computer 200 to medical personnel records computer 102. The user will also provide a set of rules that govern access to the medical personnel data associated with the user 508.

At this point, the user can log in and access 510 the medical contracts computer 400 to view the plurality of contracts 504. If the user identifies a medical contract that the user would like to select, the user selects the contract. In one configuration, the user can then access medical personnel records computer 102 and specifically authorize 511 a particular medical facility to access the medical personnel data associated with the user. Alternatively, the act of selecting the contract could act as the authorization allowing the medical facility associated with the selected contract to access the medical personnel data associated with the user. The selection generates a notification 512 that is transmitted from the medical contract computer 400 to medical facility computer 300. This automatic notification will indicate the contract selection and include information identifying the user. From this information the medical facility computer 300 can then send a request to access information 514 associated with the medical worker that has selected the proposed contract.

Once the request for information is received, the medical personnel records computer 102 will look at the rules set up by the user. This could be in one configuration, whether the user specifically authorized 511 the access, or whether the user has set up automatic authorization to follow the selection of a contract. In any event, the medical personnel records computer 102 will either allow based on the rules defined by the user.

If the medical facility has authorization to view the medical personnel data associated with the user, medical personnel records computer 102 will provide access to the requested data 516. In addition, medical personnel records computer 102 can look at the set of rules provided by the medical facility and provide the data (as long as the user rules are first satisfied) in the format the medical facility desires.

If the medical facility has been provided with all of the information required and clears the medical worker to fulfill the selected contract, the medical facility computer 300 can then generate 518 a medical credential 520 for the user that will be valid for the duration of the contract period. The step of generating the credential 540 could include automatically creating a badge that is printed out to be worn by the medical worker for the duration of the contract.

Figure 3:
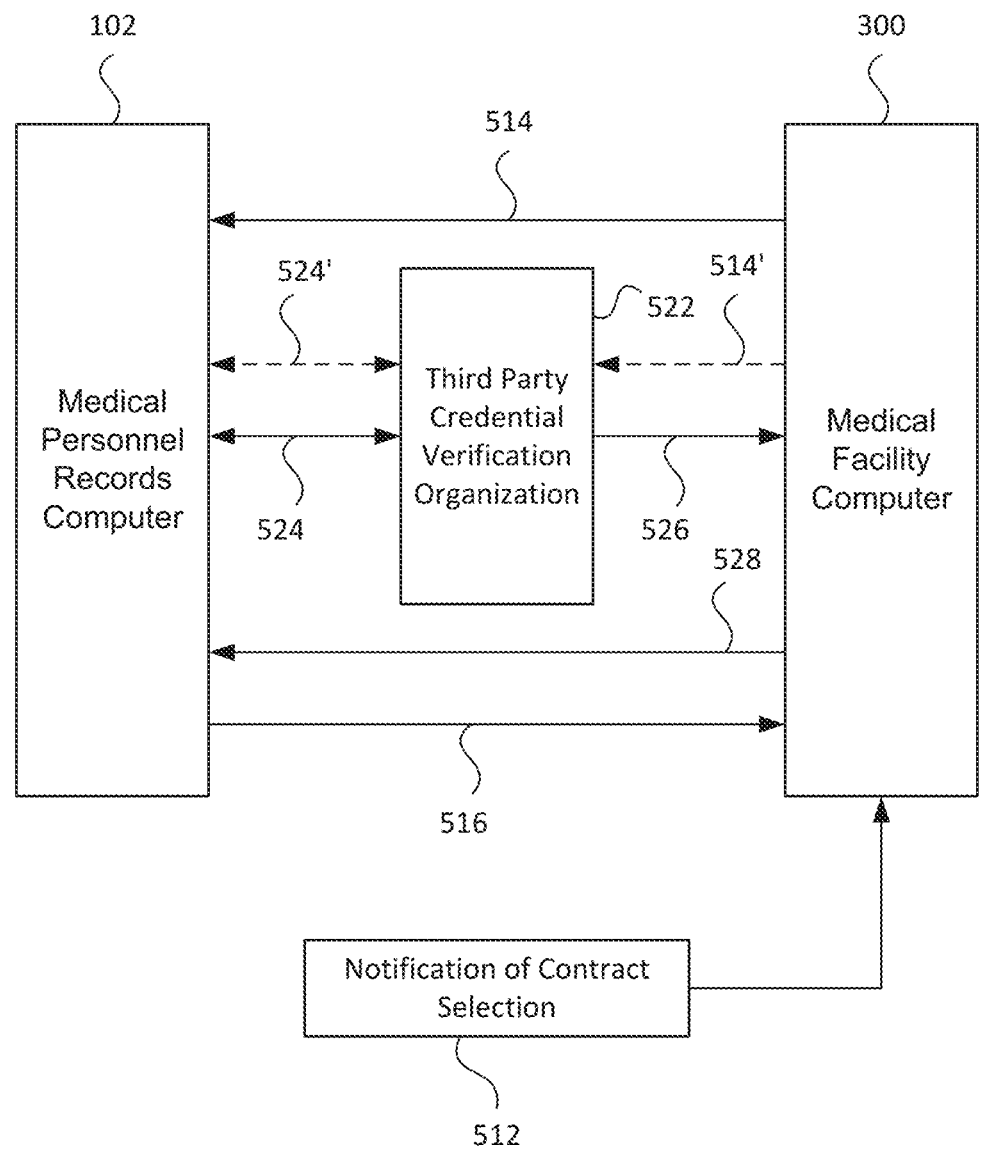
FIG. 3 is a block diagram expanding the functioning of the system according to FIG. 2.

Turning now to FIG. 3, an expanded description of the process of validating the medical personnel data associated with the user. As discussed in connection with FIG. 2, once a contract selection is made, this is selection is transmitted to medical facility computer 300. Medical facility computer 300 then sends a request to access medical personnel data associated with the user 514 that will include requests for specific data needed for the contract selected. The medical personnel records computer 102 will allow access to the requested information as long as the user defined rules are satisfied. However, a third party credential verification organization 522 is illustrated in FIG. 3. The third party credential verification organization 522 is an independent organization the medical facility can engage to verify the credentials of the user. In one configuration, the request to access medical personnel data associated with the user 514 may include data instructing the medical personnel records computer 102 to allow third party credential verification organization 522 to access the requested data 524. The third party credential verification organization 522 will then perform the task of verifying the data provided and if verified, will then transmit a verification 526 to medical facility computer 300 that the data is verified and accurate. The medical facility computer 300 can then access the medical personnel data associated with the user 528, which will in turn be accessible 516 by medical facility computer 300.

Also depicted in FIG. 3 are dashed line arrows, which illustrate an alternative method of the verification process. For example, rather than sending the request to access medical personnel data associated with the user 514 to medical personnel records computer 102, a request 514' could be transmitted to third party credential verification organization 522, which in turn, requests access to the medical personnel data associated with the user 524'. This information is verified and the verification 526 is then transmitted to medical facility computer 300 that the data is verified and accurate.

Figure 4:
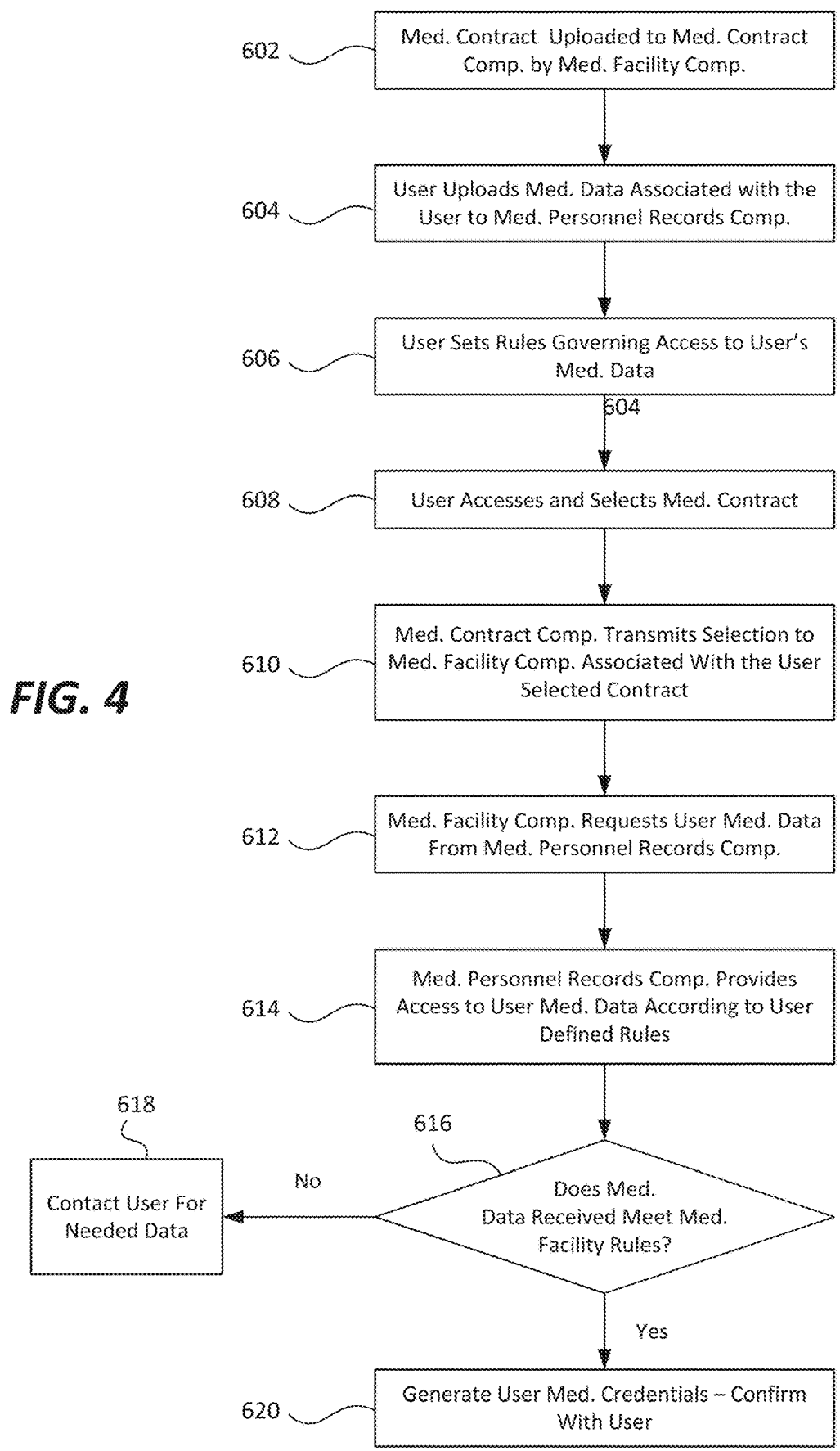
FIG. 4 is a flow diagram according to FIG. 1.

Turning now to FIG. 4, a flow and decision diagram is provided illustrating the processes followed by the system 100 in one configuration.

Initially a Medical Contract is Uploaded to Medical Contract Computer by a Medical Facility Computer 602. A User Uploads Medical Data Associated with the User to Medical Personnel Records Computer 604. Additionally, the User Sets Rules Governing Access to User's Medical Data 606. Once these preliminary steps are completed, the User Accesses and Selects a Medical Contract 608. From that point, the Medical Contract Computer proceeds to Transmit the Selection to a Medical Facility Computer Associated With the User Selected Contract 610.

The method then advances to the step of the Medical Facility Computer Requests User Medical Data From Medical Personnel Records Computer 612. The Medical Personnel Records Computer will then Provide Access to the User Medical Data According to User Defined Rules 614. It should be understood that the verification of the information provided and described in connection with FIG. 3 could occur at this point. Assuming the information is verified and acceptable, the system will then determine whether Medical Data Received Meets the Medical Facility Rules 616. If not, the system will proceed to Contact the User for Needed Data 618. If the data does meet the Medical Facility rules, the system proceeds to the step of Generate User Medical Credentials—Confirm With User 620.

A major advantage of the present system and method of allowing access to itinerate medical workers personal data is the increased security. Previous methods include the transmission of data via email or the like without any ability to automatically adjust the data provided to meet the needs of the medical facility. Likewise, the restriction of access is controlled by the user as the data is allowed to be accessed for only a certain period of time while the data is verified and then automatically provides for the generation of verified credentials. The data is not saved on the medical facility computer and cannot be accessed after a specified period of time. As such, even if a data breach were to occur at the medical facility, the opportunity for the user's data to be compromised is very small.

It is contemplated that upon user registration with the medical personnel records computer 102, a "Terms and Conditions" agreement will be executed by the user. In addition, a "Privacy" agreement will be signed by user at the time their unique links are created, but before they are sent. The links may, in one configuration, be generated by the user having a lifespan chosen by the user. The duration the system links will be active can vary, but may be in one embodiment, selected from 24 to 72 hours. It is, however, contemplated that virtually any length of time may be selected. The links provided may require a password to be accessed. The application allows for the user to create a profile and follows a common flow of documentation needed for credentialing.

As an additional feature, once all the user's information has been entered and saved to the storage 104, the user will have the option to create a Curriculum Vitae (CV) which can be included with the uploaded forms that will be sent to a recipient medical facility.

It should be noted that, while various functions and methods have been described and presented in a sequence of steps, the sequence has been provided merely as an illustration of one advantageous embodiment, and that it is not necessary to perform these functions in the specific order illustrated. It is further contemplated that any of these steps may be moved and/or combined relative to any of the other steps. In addition, it is still further contemplated that it may be advantageous, depending upon the application, to utilize all or any portion of the functions described herein.

FIGS. 5-13 are illustrated screen shots of some of the webpages on the medical personnel records computer 102 that can be used to upload personal medical information associated with the user.

Figure 5:
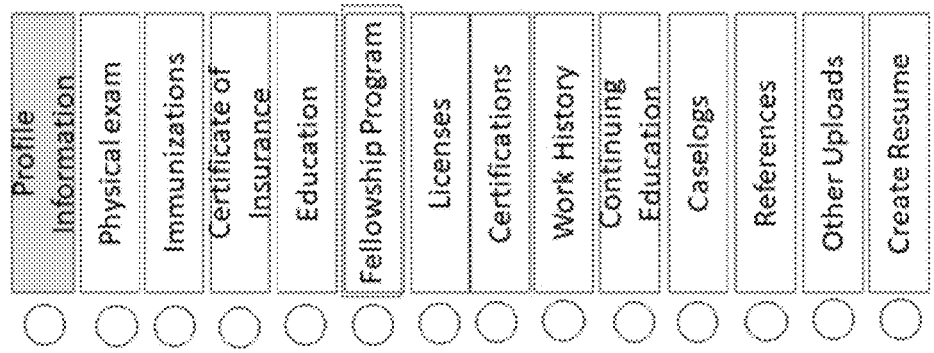

FIG. 5 illustrates a menu of options where Profile Information has been selected. The webpage allows for the input of the user's name, address, profile information and passport picture. All of this information is required for medical credentialing.

FIG. 6 illustrates a menu of options where Physical Examination has been selected. There are various formats that this information can be provided in, including for example, a text format or an image format.

Figure 7:
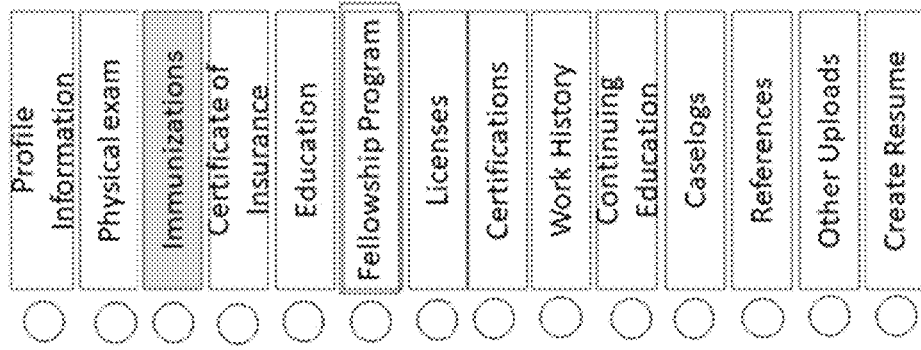

FIG. 7 illustrates a menu of options where Immunization Information has been selected. This information could include for example, Titers, Flu Shot, PPD and other immunization records.

Figure 8:
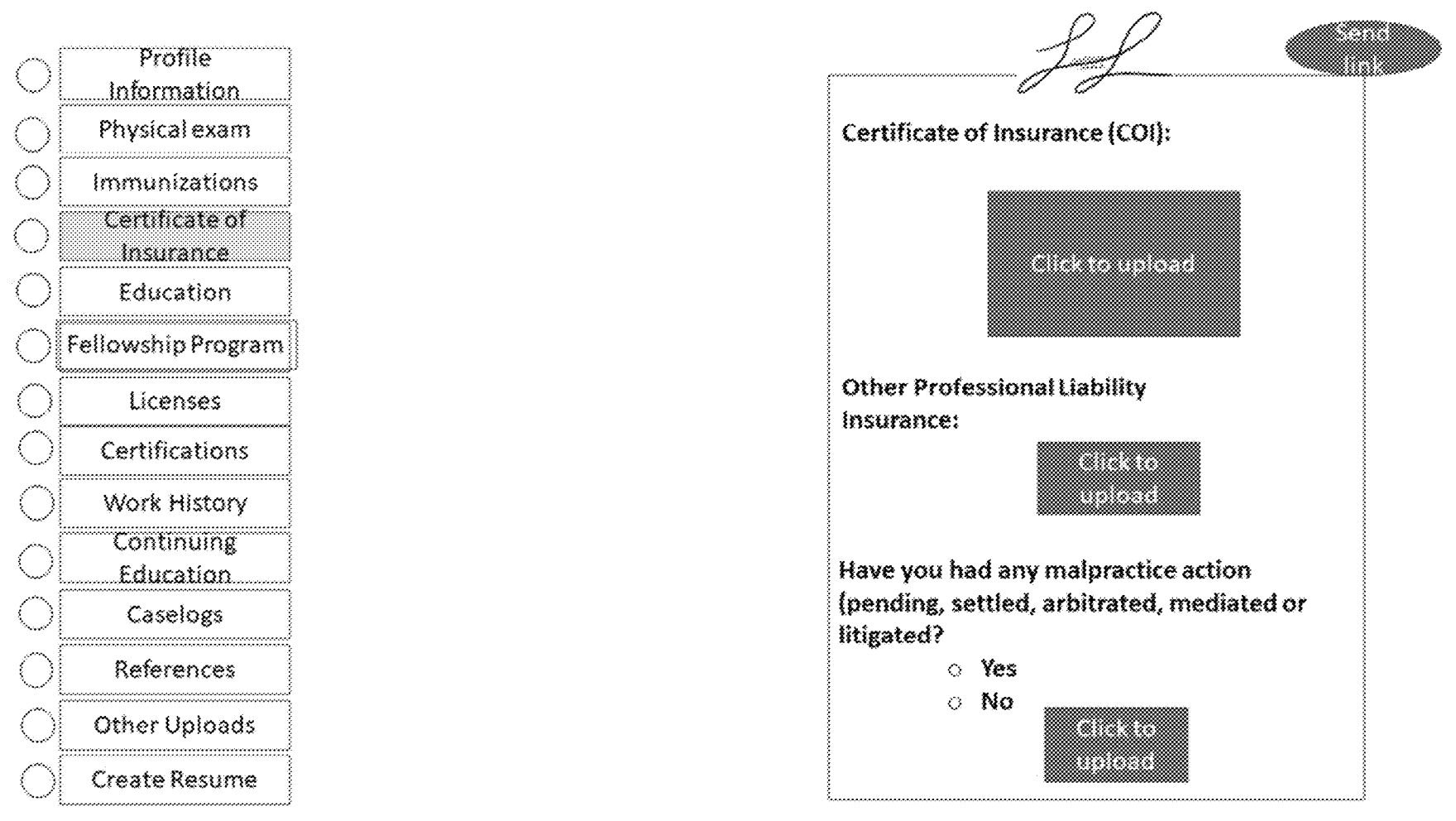

FIG. 8 illustrates a menu of options where Certificate of Insurance has been selected. This information could include for example, malpractice insurance including letters of verification, liability insurance, and data relating to insurance claims and the like.

Figure 9:

FIG. 9 illustrates a menu of options where Education History has been selected. This information could include for example, undergraduate transcripts including a copy of the undergraduate diploma, graduate transcripts including a copy of the graduate diploma, fellowship training, and the like.

Figure 10:
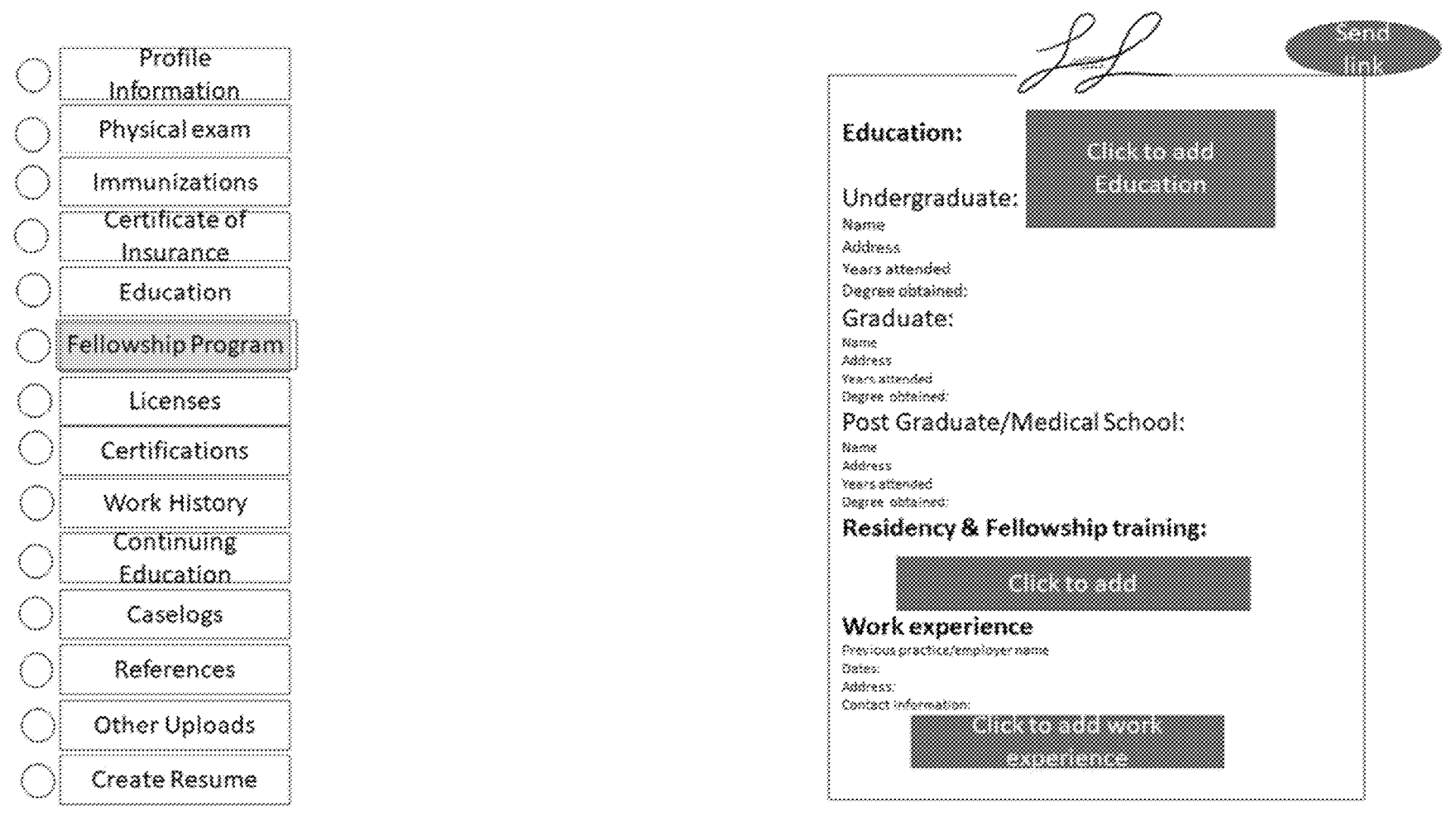

FIG. 10 illustrates a menu of options where Fellowship/Residency has been selected. This information could comprise any and all information showing completion of any fellowships and/or residency.

Figure 11:
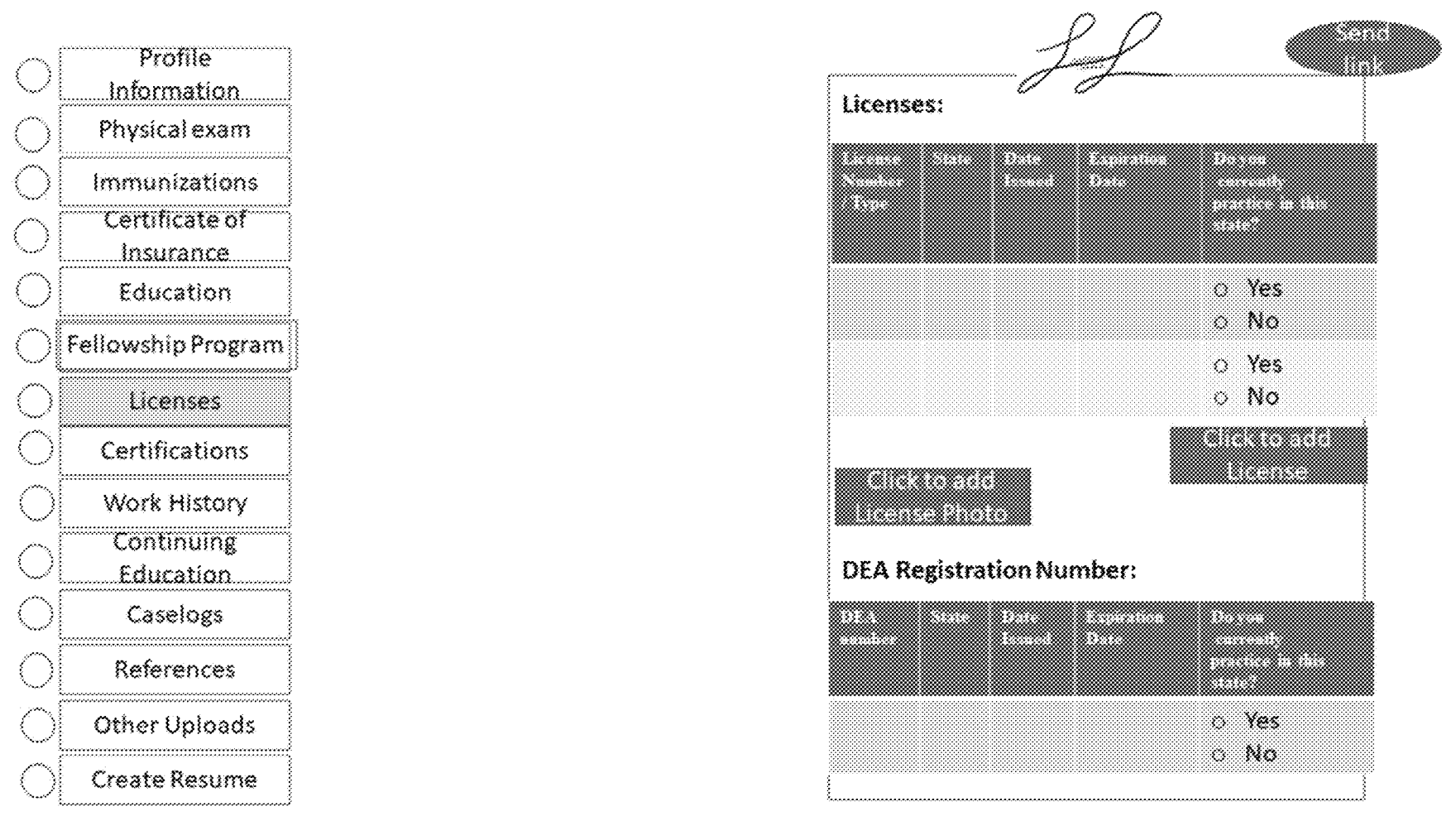

FIG. 11 illustrates a menu of options where Licenses has been selected. This information could include a listing of all medical licenses listed by state and including the license number, the year issued and the expiration date.

FIG. 12 illustrates a menu of options where Certifications has been selected. This information could include among other certifications, Advanced Cardiac Life Support (ACLS), Pediatric Advanced Life Support (PALS), Basic Life Support (BLS), Neonatal Resuscitation Program (NRP), various Trauma certifications, Board Certification/Membership Cards and any other certifications.

FIG. 13 illustrates a menu of options where Work History has been selected. This information could quite lengthy including the facility name, date of employment, address for the medical facility and contact information. It is contemplated that as work contracts are accepted and completed, the system could automatically update this section for the user. For example, at the date of completion of the work contract or at another date (e.g. when the user logs back into medical personnel records computer 102) the system could automatically prompt the user as to whether the contract was successfully completed and whether the user's work history should be updated. Upon confirmation, the system could enter all the information from the previous work contract, which could be received from the medical contracts computer 400 or from the medical facility computer 300.

Other screens could include for example, Continuing Education information, Case logs information, and Reference information. The above are provided to further illustrate the type of information the user may provide to medical personnel records computer 102 and may want to be received by medical facility computer 300 prior to generating credentials to fulfill a selected contract.

Additionally, once all of the user's information has been entered into the system 100, the user has the option to create a Curriculum Vitae (CV), which can be included with the uploaded forms that will be sent to the recipient and would be assembled based on the information provided by the user. Additionally, it is contemplated that the resume builder application could automatically update and continue building the user's resume as various work contracts are selected and fulfilled.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for selectively controlling access to medical personnel data comprising:
    a medical personnel records computer having a storage and coupled to a network;
    said medical personnel records computer adapted to receive medical personnel data associated with a user and saved on the storage, the user setting user defined rules governing access to the medical personnel data associated with the user;
    wherein a medical contract computer having a plurality of proposed medical contracts each associated with a medical facility saved thereon is accessible by a user via a user computer via the network;
    wherein upon selection of at least one of the plurality of proposed medical contracts, said medical contract computer couples to a medical facility computer associated with the selected medical contract, said medical contract computer transmitting data relating to the user selected contract and the user;
    wherein the medical facility computer couples to said medical personnel records computer in response to receipt of the data relating to the user selected contract and the user, the medical facility computer having medical facility defined rules;
    said medical personnel records computer selectively allowing access to the medical personnel data associated with the user for only a defined time period according to the user defined rules;
    said medical personnel records computer presenting medical personnel data associated with the user to the medical facility computer based on the user defined rules and the medical facility defined rules.

2. The system according to claim 1 wherein time period is selectable in a range from between 24-72 hours.

3. The system according to claim 1 wherein the medical facility defined rules are programmable and govern a format of the medical personnel data that is presented to the medical facility computer.

4. The system according to claim 3 wherein the medical facility defined rules govern the type of medical personnel data associated that is presented to the medical facility computer based on a location of the medical facility.

5. The system according to claim 4 wherein the type of medical personnel data is selected from the group consisting of: education information, licensing information, certification information, insurance information, malpractice information, immunization information, health status information and combinations thereof.

6. The system according to claim 1 wherein said medical personnel records computer utilizes certificate-based encryption in connection with the medical personnel data that is presented to the medical facility computer.

7. The system according to claim 1 wherein presenting medical personnel data associated with the user to the medical facility computer includes transmission of the medical personnel data from the medical personnel records computer to the medical facility computer in a file wherein the file is only accessible by the medical facility computer for the defined time period.

8. The system according to claim 1 wherein medical credentials for the user are automatically generated when the received medical personnel data associated with the user is compliant with the set of rules for the medical facility.

9. The system according to claim 8 wherein the automatic generation of medical credentials further includes creating a badge that is wearable by the user.

10. A method for selectively controlling access to medical personnel data comprising the steps of:
  accessing a medical personnel records computer and uploading medical personnel data associated with a user to be saved on a storage accessible by the medical personnel records computer;
  setting user defined rules governing access to the medical personnel data associated with a user;
  accessing a medical contract computer having a plurality of proposed medical contracts each associated with a medical facility;
  selecting at least one of the plurality of proposed medical contracts;
  transmitting the selection from the medical contract computer to a medical facility computer associated with the medical contract selected by the user;
  requesting medical personnel data associated with a user be accessed by the medical facility computer;
  granting the access request of the medical facility computer to access the medical personnel data associated with a user when the user defined rules allow for such access; and
  generating medical credentials when the accessed medical personnel data associated with a user is compliant with a medical facility defined set of rules.

11. The method according to claim 10 wherein the user defined rules set a time period within which the medical facility computer may access the medical personnel data associated with the user.

12. The method according to claim 11 wherein time period is selectable in a range from between 24-48 hours.

13. The method according to claim 10 wherein said medical facilities computer transmits the medical facility defined rules to the medical personnel records computer, and wherein the medical personnel data associated with the user is presented to the medical facility computer based on the user defined rules and the medical facility defined rules.

14. The method according to claim 13 wherein when the user defined rules conflict with the medical facility defined rules, the user defined rules control.

15. The method according to claim 10 wherein said medical facilities computer includes programmable medical facility rules that govern a format of data to be received from the medical personnel data computer such that the medical personnel data associated with the user is presented to the medical facility computer in a format defined by the medical facility rules.

16. The method according to claim 15 wherein medical facility rules govern a type of medical personnel data associated with the user that is presented to the medical facility computer.

17. The method according to claim 16 wherein the type of medical personnel data is selected from the group consisting of: education information, licensing information, certification information, insurance information, malpractice information, immunization information, health status information and combinations thereof.

18. The method according to claim 10 wherein the medical personnel records computer utilizes certificate-based encryption in connection with the medical personnel data that is accessed by the medical facility computer.

19. The method according to claim 10 wherein the step of generating medical credentials is performed automatically when the accessed medical personnel data associated with a user is compliant with a medical facility defined set of rules.

20. The method according to claim 19 further comprising the step of creating a badge that is wearable by the user.

* * * * *